(12) United States Patent
Sarvazyan (10) Patent No.: US 7,947,001 B1
(45) Date of Patent: May 24, 2011

(54) METHODS AND DEVICES FOR MEASURING STRUCTURAL AND ELASTIC PROPERTIES OF A HOLLOW ORGAN

(76) Inventor: Armen P. Sarvazyan, Lambertville, NJ (US)

( * ) Notice: Subject to any disclaimer, the term of this patent is extended or adjusted under 35 U.S.C. 154(b) by 0 days.

(21) Appl. No.: 12/794,955

(22) Filed: Jun. 7, 2010

(51) Int. Cl.
*A61B 5/117* (2006.01)
*A61B 5/103* (2006.01)

(52) U.S. Cl. ..................................... 600/587

(58) Field of Classification Search .................. 600/587, 600/505, 509, 424, 207, 463; 606/192
See application file for complete search history.

(56) References Cited

U.S. PATENT DOCUMENTS

| | | | |
|---|---|---|---|
| 4,776,347 A | 10/1988 | Matthews | |
| 5,275,169 A | 1/1994 | Afromovitz | |
| 5,924,984 A | 7/1999 | Rao | |
| 6,447,462 B1 | 9/2002 | Wallace et al. | |
| 6,743,165 B2 | 6/2004 | Mosel | |
| 2004/0147811 A1* | 7/2004 | Diederich et al. | 600/207 |
| 2005/0124920 A1 | 6/2005 | Gregersen | |
| 2007/0015994 A1 | 1/2007 | Hong | |
| 2007/0083126 A1* | 4/2007 | Marko et al. | 600/505 |
| 2007/0167823 A1* | 7/2007 | Lee et al. | 600/463 |
| 2008/0027358 A1 | 1/2008 | Gregersen | |
| 2010/0305429 A1* | 12/2010 | Shachar et al. | 600/424 |

* cited by examiner

Primary Examiner — Max Hindenburg
Assistant Examiner — Brian Szmal
(74) Attorney, Agent, or Firm — Boris Leschinsky (57) ABSTRACT

A spatial profile of structural and elastic parameters along a lumen of a hollow organ is determined based on obtaining the functional dataset of pressure P, balloon volume V, and balloon linear coordinate X while continuously moving the balloon along the lumen. A comprehensive characterization of elastic properties of the tissue and geometrical parameters of the lumen are then determined using a previously obtained calibration curve of balloon pressure vs. balloon volume when the balloon is expanded freely. As opposed to prior art devices for measuring tissues elasticity at one or several distinct locations by having deploying a balloon locally, the present invention describes a device in which the balloon is continuously moved through the lumen of the hollow organ whereby allowing elasticity determination over a significant portion or the entire length of the organ. The relationship between P, V, and X is then described by a family of constant pressure curves $F(P_i=\text{const},V,X)$, in the constant pressure method; or by family of constant volume curves $F(P, V_i=\text{const},X)$, in the constant volume method. The handheld device of the invention supports evaluation using either method. Repeating the test at different levels of balloon pressure or volume allows obtaining of a family of curves characterizing linear distribution of wall compliance along the lumen. Methods and devices of the invention can be used to evaluate cervix, urethra, esophagus, intestines, blood vessels, and other organs.

9 Claims, 12 Drawing Sheets

METHODS AND DEVICES FOR MEASURING STRUCTURAL AND ELASTIC PROPERTIES OF A HOLLOW ORGAN

BACKGROUND OF THE INVENTION

1. Field of the Invention

The present invention relates generally to medical diagnostic devices and methods. More particularly, the invention discloses methods and devices for characterization of a hollow organ by moving a balloon-tipped catheter through an internal lumen of such organ. Tissue elasticity, compliance, or distensibility distribution along the lumen as well as its diameter variations are some examples of what can be measured using the present invention.

A physiologic function of many organs and systems in the body depends on their mechanical and geometrical properties. Gastrointestinal tract, urinary tract, breathing and reproductive systems as well as blood vessels and the circulatory system in general are just some examples of physiological systems containing hollow organs and lumens that may need such characterization. The following description provides some examples in which using the present invention may be advantageous.

Gastrointestinal tract. Biomechanical properties of the large and small intestine in-vivo are largely unknown, despite the fact that their distensibility is important for normal function, and altered mechanical properties are associated with gastrointestinal (GI) diseases. Data in the literature pertaining to mechanical aspects of GI function are concerned with the contraction patterns, the length-tension relationship in circular and longitudinal tissue strips in vitro, flow patterns, the compliance and the stress-strain relationship. Traditionally used methods for clinical or basic investigations of the GI tract are endoscopy, manometry and radiographic examinations. Although these methods provide useful diagnostic information, they do not assess tissue biomechanical parameters which could be important for characterization of the state and functionality of the organ.

Obstructive diseases of the rectosigmoid region including anorectal canal and rectum may include various growths and polyps that impact the wall elasticity of these organs. Both passive and active evaluations of this region (active evaluation describes the evaluation in the presence of conscious or involuntary muscle contraction) may allow for diagnosis and management of the anal incontinence and other diseases.

Proper catheter-based minimally invasive tools are needed to allow mechanical compliance characterization of various sections of the GI tract.

Lower esophagus. Studying the gastroesophageal junction and in particular the lower esophageal sphincter is often necessary to diagnose various esophageal disorders such as gastroesophageal reflux disease, stricture, achalasia, diffuse esophageal spasm, esophageal cancer and dysphagia. These esophageal disorders affect the ability of the sphincter to open and close normally. The sphincter rests in a closed position to shut off the end of the esophagus, and is relaxed when in the open state. However, the sphincter does not have the ability to open on its own; rather it opens briefly by normal physiological function of the esophagus during excitation of the inhibitory nerves of the esophagus. New methods and devices are needed for comprehensive characterization of the elasticity of the lower esophagus and the sphincter in order to diagnose its various anomalies and diseases.

Urinary tract. Many organs and lumens of the male and female urinary system are in need of mechanical characterization. Urethral and prostate mechanical properties in men play a critical role in the diagnosis and management of prostate enlargements, both benign and malignant. Prostate enlargement affects the stiffness and elasticity of the urinary tract in its vicinity. Evaluation of the urinary tract compliance allows for indirect and minimally invasive diagnosis of prostate enlargement.

Male and female urge and stress incontinence involve various portions of the bladder and lower urinary tract organs. While urodynamics evaluations allow for diagnosis of many aspects of these conditions, elasticity of the urinary tract organs have not been studied to a degree allowing its inclusion in the standard series of tests for patients with incontinence complaints.

Reproductive system. The cervix is the lower portion of the uterus. It is composed of fibrous tissue and its mechanical integrity is crucial for maintaining a healthy gestation. During normal pregnancy, the cervical extracellular matrix remodels in preparation for labor. To date no diagnostic tool is yet available to objectively assess the in-vivo biomechanical properties of the uterine cervix during gestation in order to objectively detect or confirm the onset of cervical insufficiency or premature labor leading to a preterm birth of a baby.

Circulatory system. Atherosclerosis is a global disease affecting both coronary as well as peripheral blood vessels. Sophisticated imaging techniques have been developed in recent years allowing characterization of blood vessels and detecting of anomalies associated with plaque deposits on their walls. Development of comprehensive examination methods for compliance assessment of blood vessels will further improve diagnostic accuracy and clinical decision making as to proper intervention when plaque deposits are identified.

In addition to plaque deposits, various other diseases cause flow restriction throughout the circulatory system, such as aortic stenosis or vascular spasms. Compliance evaluation of various blood vessels will open new opportunities for diagnosis and management of various cardiovascular diseases.

Elasticity assessment tools and methods of the prior art involve generally a catheter or a tube equipped with a single or a series of inflatable balloons. The catheter is placed in the lumen of a hollow organ or vessel and balloons are inflated to push against the wall of the lumen. Pressure-volume curve is then created characterizing the wall of the lumen and its surrounding organs at that location. This general approach works well for spot-checking of elasticity. However, many diseases are extended throughout the length of the lumen and therefore are not amenable for evaluation using these devices.

2. Description of the Background Art

Numerous patents and patent application describe use of inflatable tools inserted in a hollow organ of the human body in order to obtain the mechanical response from the surrounding tissues and to estimate their mechanical, geometrical and functional characteristics. A cuff inflatable by air combined with a pressure gauge was proposed for monitoring sphincter type muscles (U.S. Pat. No. 4,776,347). Multiple pressure sensors with a stimulus balloon were aimed to measure muscle activity in the anorectal canal (U.S. Pat. No. 5,924,984). Disposable infusion balloon-tipped catheters in connection with pressure monitoring sensors were proposed for measurements of physiological pressure in the urinary system (U.S. Pat. No. 6,447,462) and for estimations of particular pressure, internal cross-section and diameter of blood vessels basing on the balloon fluid pressure (U.S. Pat. No. 5,275,169). Pressure-volume and force-deformation relationships of inflatable balloons can be used for calculation of morphometric parameters of hollow organs, such as the wall thickness (US Pat. Appl. 2008/0027358), active and passive elastic properties of muscle walls (US Pat. Appl. 2005/0124920), urinary incontinence parameters (US Pat. Appl. 2002/0111586), biomechanical parameters of esophagus (US Pat. Appl. 2007/0015994), etc.

The present invention is aimed at significant innovative enrichment of the methods of measuring structural and biomechanical parameters of hollow organs using inflatable balloons and relationship between pressure-volume increments by introducing axial profiles of elasticity built on the basis of a plurality of records along the examined organ at different levels of straining.

SUMMARY OF THE INVENTION

Accordingly, it is an object of the present invention to overcome these and other drawbacks of the prior art by providing novel methods and devices for comprehensive assessment of structural and elastic properties of a hollow organ with a lumen traversing therethrough.

It is another object of the present invention to provide methods and devices for determination of structural and elastic properties of a hollow organ in its relaxed state (passive evaluation) and when it is under load or tension (active evaluation).

It is a further object of the present invention to provide methods and devices for measuring structural and elastic properties of a hollow organ over an extended length throughout its internal lumen.

It is yet a further object of the present invention to provide a methods and devices for measuring structural and elastic properties of a hollow organ as well as its surrounding organs and tissues while scanning along said organ.

The methods and devices of the invention are based on continuously moving of a balloon-tipped catheter through the lumen of a hollow organ while injecting fluid into or withdrawing fluid from the balloon. Three key parameters are measured at the same time: position of the balloon inside the organ, fluid pressure inside the balloon, and balloon volume equal to infused fluid volume inside the balloon. As opposed to elasticity-measuring devices of the prior art having a statically deployed balloon, the present invention describes a device in which the examination is conducted in the scanning mode and balloon is continuously moved through the lumen of the hollow organ, whereby allowing determination or structural and elastic properties over a significant portion or the entire length of the organ. Investigation of a hollow organ by one of the innovative modalities proposed by the invention, namely the constant pressure method or the constant volume method, results in obtaining a pressure/volume/linear coordinate data set, on the base of which topographical profiles along the organ of the mechanical (elastic modulus), structural (wall thickness) and geometrical (lumen diameter and area) parameters are calculated. The profiles allow localization within the organ of areas of pathological narrowing or enlargement of the lumen, softening or stiffening of walls tissue, as well as appearance of pathological inclusions of altered elasticity. The invention includes designs for portable handheld devices used for example in urology for examination of the males' urinary tract and prostate for the presence of cancer and prostatitis, gynecology and obstetrics for diagnostics of the cervix insufficiency during gestation, gastroenterology, diagnostics of the cardiovascular system and other biomedical applications.

BRIEF DESCRIPTION OF THE DRAWINGS

A more complete appreciation of the subject matter of the present invention and the various advantages thereof can be realized by reference to the following detailed description in which reference is made to the accompanying drawings in which.

DETAILED DESCRIPTION OF THE PREFERRED EMBODIMENTS OF THE INVENTION

A detailed description of the present invention follows with reference to accompanying drawings in which similar elements are indicated by reference letters and numerals.

Figure 1:
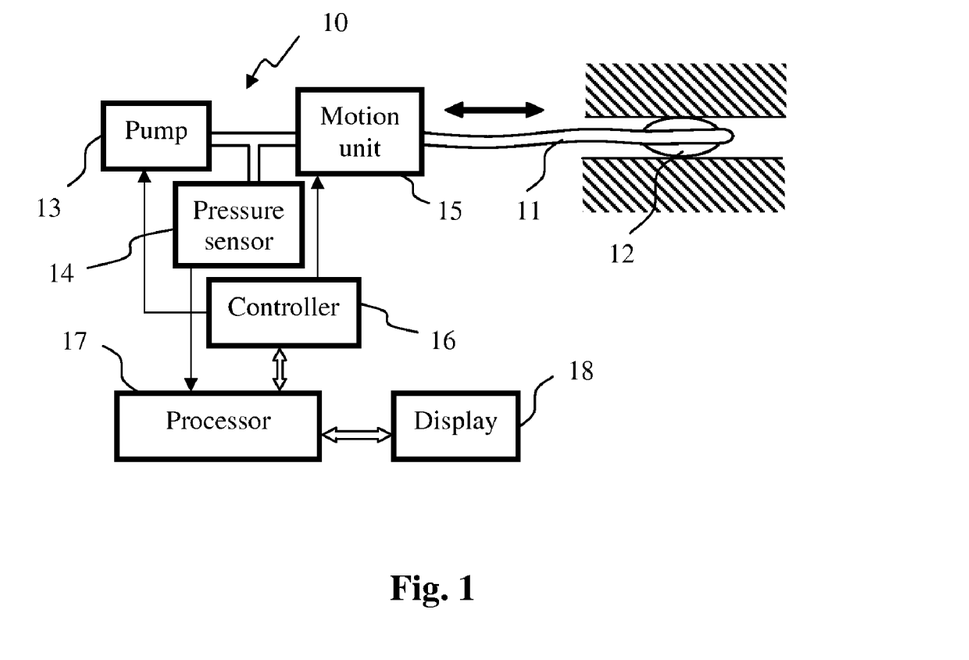
FIG. 1 is a general schematic layout showing principal components of the system and their functional interaction.

The method of invention is based on monitoring and recording of three parameters during examination act: balloon pressure P, fluid volume V and balloon linear position X along a hollow organ of the body. This allows generating a spatial profile of elasticity, Young's modulus and other parameters along a selected portion of the length of the lumen. FIG. 1 generally shows the principle layout of the apparatus 10 designed to achieve this objection. It is shown with a catheter interacting with a lumen 100 of the hollow organ under examination. The lumen 100 may be for example a cervix or a section of the urethral channel traversing a prostate gland. The following description however is applicable to many other hollow organs in the body including esophagus, intestines, blood vessels, etc. A catheter 11 with an inflatable balloon 12 located close to its distal tip is placed in the lumen of the hollow organ 100. The catheter is adapted to allow for motion of the balloon within the lumen in both directions. A volume control unit 13 regulates desired pressure or volume of inflated liquid substance within the balloon 12 and is adapted to inject and withdraw controlled amounts of fluid in and out of balloon 12. This system can include a positive displacement pump such as for example a variable volume chamber made using a piston-in-a-cylinder or bellows and driven by an auxiliary linear actuator. Balloon volume is monitored internally in the control unit based on the volume of injected fluid, which is calculated based on a known diameter of the bellows or piston and a measured stroke length equal to the known displacement of the linear actuator. As can be appreciated by those skilled in the art, other variable volume fluid injection and withdrawal systems can be used for the purposes of the present invention including a motor-driven fluid-filled syringe, roller pump, diaphragm pump etc.

Pressure within the catheter 11 and, consequently, inside the balloon 12 is continuously monitored using a pressure sensor 14. Motion unit 15 performs controlled displacement of the catheter 11 along the lumen of the hollow organ 100 according to a measurement algorithm. The motion unit 15 adapted to move the catheter 11 in the both directions can include a linear ball-screw actuator or another known mechanism.

Control unit of the apparatus 10 includes a controller 16 that manages operation of the pump 13 and the motion unit 15, as well as a processor 17 adapted to issue commands to the controller 16 and accept data from the pressure sensor 14 and other sources, and a display 18 for presentation of results.

Figure 2:
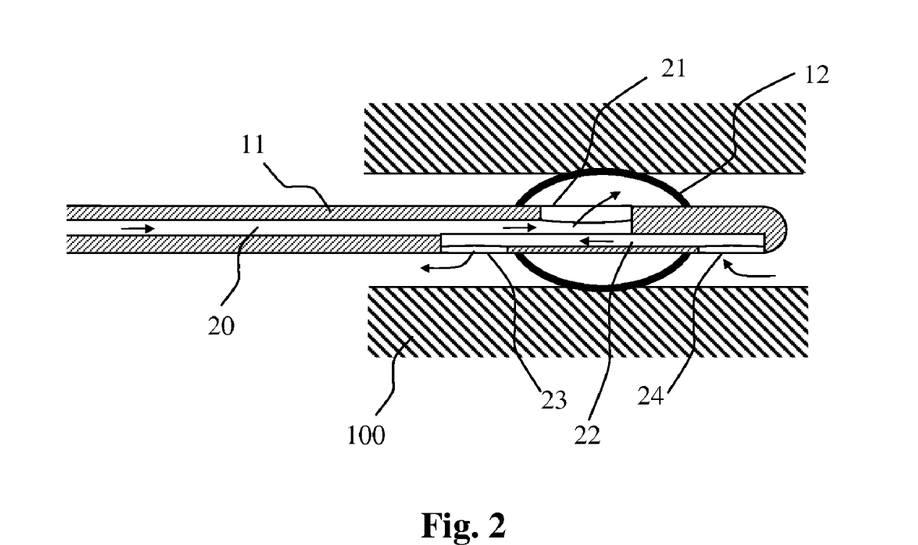
FIG. 2 is a schematic view of a catheter tip with an inflatable balloon, inserted in the lumen of a hollow organ of the body.

A detailed view of structure of the distal tip of the catheter 11 with the inflatable balloon 12 positioned within the lumen 100 is shown in FIG. 2. The outer diameter of the catheter 11 in its widest section (such as at balloon 12 when it is deflated) is selected to be less than the lowest anticipated diameter of the lumen 100 (such as when it is under tension or spasm) so as to assure the ability of the catheter 11 to be moved freely along the lumen 100. At the same time, it is desirable to provide the largest available cross-section inside the catheter passage so as to reduce resistance for fluid infusion and withdrawal to and from the balloon 12. Material selection for the catheter 11 and the balloon 12 is important to assure its sufficient flexibility to be able to reach the target area through a possibly tortuous insertion pathway. The outer diameter of the balloon 12 when inflated at the maximum inflation pressure is preferably selected not to exceed the safe limit for lumen 100 extension so as not to cause trauma to the target organ. The values of the highest safe inflation pressure and the highest allowable balloon diameter when inflated are selected based on individual characteristics of the target organ. The length of balloon 12 is selected to be less than the length of the target lumen of interest. A specific example of a catheter of the invention useful for evaluation of prostate would be an 8 Fr or 10 Fr single lumen silicone tube having a 3 cc latex balloon at its distal end. One or more openings 21 allow fluid communication to the balloon 12 through the catheter 11. The size of the inner channel 20 of the catheter 11 and opening 21 at its distal end are selected appropriately to provide fast inflation and deflation of the balloon 12 by the pump 13. The catheter 11 may have an additional bypass channel 22 with openings 23 and 24 at its opposite ends, for example, in application to diagnostics of the circulatory system. The bypass channel 22 allows free passing of blood past the balloon 12 along a blood vessel and prevents occlusion of the vessel due to closing of the lumen by the balloon. Although catheter 11 is shown to have one inner channel 20 connected to the balloon 12, it is anticipated that multi-channel catheters may also be used for example with a secondary channel adapted for insertion of the catheter 11 over a guide wire or to monitor pressure distally or proximally to the location of the balloon 12.

Figure 3:
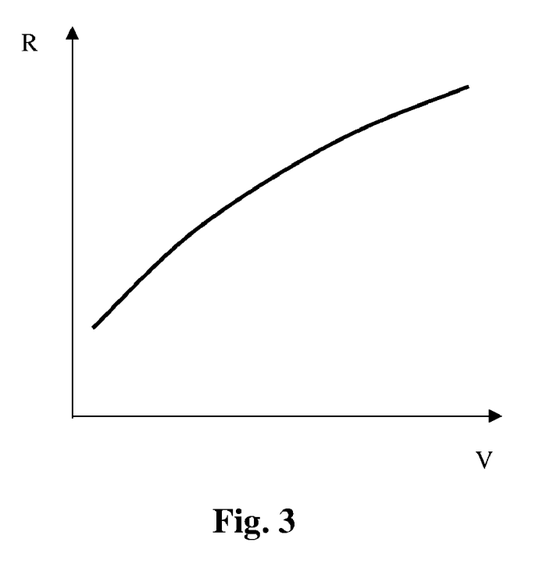
FIG. 3 shows dependence of the elastic balloon radius on the volume of fluid injected therein.
Figure 4:
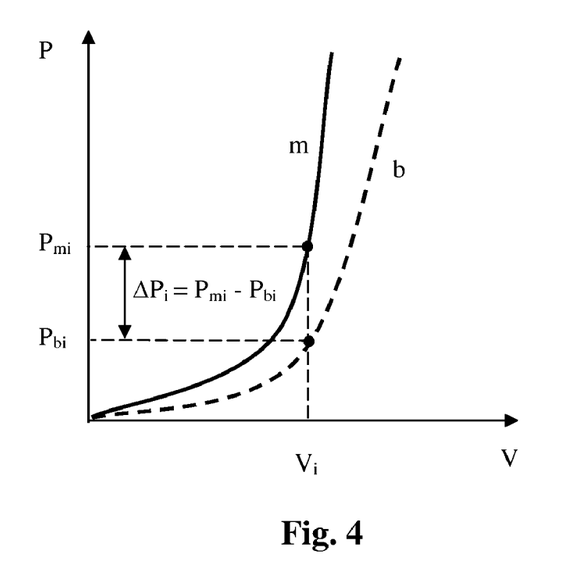
FIG. 4 is a diagram illustrating dependence of internal pressure inside the balloon on the inflated volume for unrestricted and loaded cases and determination of the additional pressure imposed by the loading.

FIG. 3 and FIG. 4 illustrate initial considerations related to the method of the invention. Radius R of a quasi-spherical balloon 12 is a function of the volume of injected liquid V that is pumped therein, but the dependence of R on V is nonlinear as shown in FIG. 3. This dependence is a function of the balloon's shape and can vary from being a function of $R^3$, if the balloon is shaped as a sphere, to the function of $R^2$ in the case it is a cylinder. The R vs. V dependence can be affected also by external loading or external pressure, but this can be ignored in the case when the balloon's own stiffness allows maintaining a constant shape.

FIG. 4 depicts pressure-volume graphs inside the inflated balloon. Two graphs are shown: graph (b) is illustrating P-V relationship without external balloon loading allowing it to expand freely and graph (m) shows the same in the presence of at least some external constraint or loading. The P vs. V functions can be approximated by a third-degree curve as shown that relates to the balloon's shape, in this case assumed to be close to spherical. The initial $P_b$ vs. V dependence should be obtained prior to the evaluation at the balloon calibration stage. This curve is used for two purposes: estimations of pressure increments for a given volume of injected fluid and for detecting maximum volume of fluid which can damage the balloon—this maximum volume should not be exceeded during evaluation procedure. Knowing graphs (m) and (b) allow determination of additional pressure $\Delta P$ as the difference between measured pressure $P_m$ in the externally loaded balloon and previously recorded $P_b$ without external loading. This is shown in FIG. 4 for a predetermined volume V. Additional pressure $\Delta P$ defines the external loading and is used for calculation of the elastic modulus of the tissue and geometric parameters of the lumen from measurements at various volumes V.

The structural and elastic properties of tissue can be measured using the system of the invention by one of two methods: 1) constant pressure P evaluation method and 2) constant volume V evaluation method. According to the constant pressure method, the system maintains a constant level of pressure P in the balloon by adjusting and measuring the volume of injected fluid V during controlled movement of the balloon through the lumen of a hollow organ. According to the constant volume method, the system maintains a constant level of volume V in the balloon during controlled movement of the balloon through the lumen of a hollow organ while monitoring pressure P therein.

According to the first method of the present invention (constant pressure P), the catheter with deflated balloon is first placed at the beginning of the target lumen section of the hollow organ. The balloon is then inflated with an appropriate fluid until pressure P within the balloon 12 reaches some level corresponding to a low force imposed to the walls of the lumen 100. The apparatus 10 is configured to maintain this level of pressure as a constant throughout the entire examination by injecting fluid in or withdrawing fluid out of balloon 12 as will be described in greater detail below.

Incompressible liquids are preferred to be used for inflating the balloon as the fluid volume and pressure are easy to determine by the sensors located at the device and away from the balloon itself. Gases can also be used if desired but in that case their compressibility has to be taken into account when determining the balloon pressure and volume.

The volume of fluid V needed to achieve the initial inflation target pressure $P_0$ will depend in part on the elasticity of the lumen wall surrounding the balloon. Highly elastic wall will cause more fluid injection to achieve the target pressure. On the other hand, stiffer lumen wall will cause less fluid volume V needed to get to the target pressure. The amount of initial fluid volume V is measured by the apparatus 10 as well as subsequent volume increments needed to maintain the pressure in the balloon 12 at the same constant level.

Figure 5:
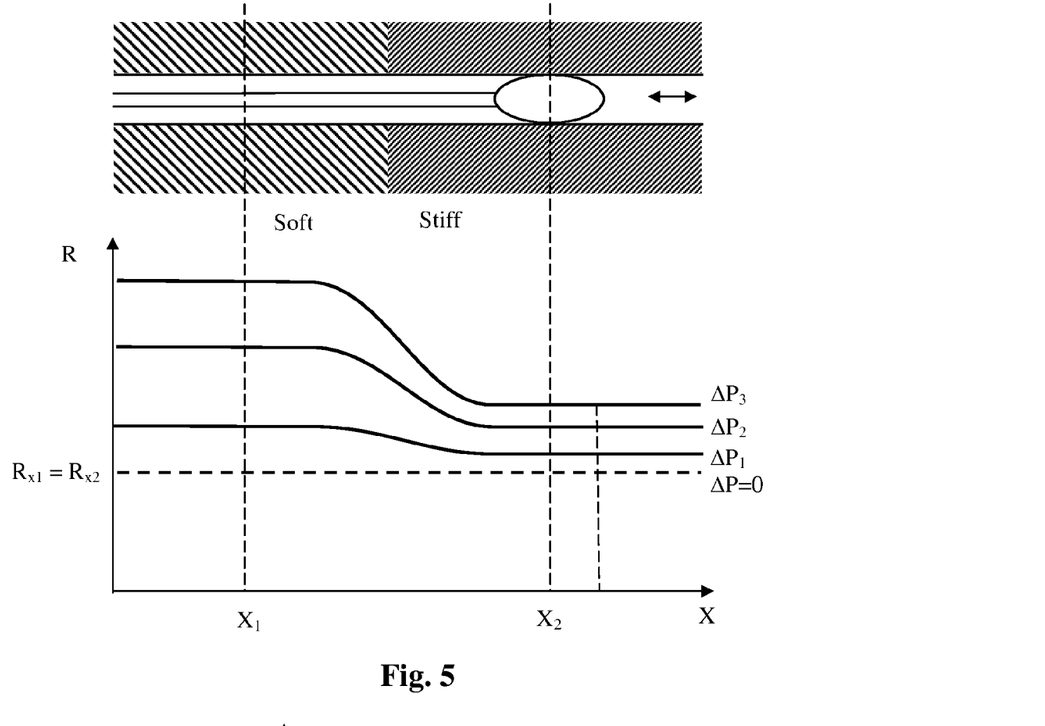
FIG. 5 is a diagram showing changes of balloon's radius during movement along a constant diameter lumen containing two areas of different wall stiffness using a constant pressure evaluation method.
Figure 6:
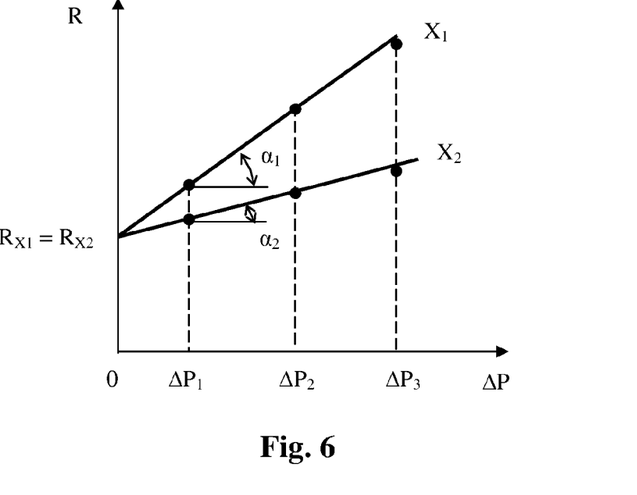
FIG. 6 is a graph of dependence of the balloon's radius on the additional pressure for evaluation circumstances shown in FIG. 5.

FIGS. 5-10 illustrate three evaluation cases using the constant pressure method. The first case shows the catheter 11 with balloon 12 being moved along the lumen of a constant diameter and having two areas of different elasticity of its walls, depicted here as soft and stiff, as illustrated in FIG. 5 (upper panel) and FIG. 6. FIG. 5 (lower panel) shows differences of the balloon radius R in soft and stiff areas at different levels of additional pressure $\Delta P$. Due to a greater compression of the balloon by the lumen's walls in the stiff area, the same level of pressure corresponds to smaller radius R in the stiff area. As a result gradually increasing pressure level, the radius increases both in soft and stiff areas, but to a greater extent in the stiff area. If the balloon enters the stiffer wall area, the inside pressure rises. The devise adaptively withdraws fluid from the balloon 12 so as to keep the pressure at the target level. If the wall of the lumen becomes softer, the pressure in the balloon 12 will correspondingly fall. Then the device is configured to infuse more fluid into balloon 12 in order to keep the pressure P at the same constant level. Importantly, at least three key parameters characterizing the movement and behavior of the balloon 12 in the lumen 100 are continuously monitored: additional pressure $\Delta P$ (which is the difference between currently measured pressure and the pressure determined while without external loading during calibration stage, see FIG. 4), fluid volume V that is injected or withdrawn from the balloon and balloon's linear movement coordinate X along the lumen 100.

For more accurate characterization of elasticity and geometry of the lumen, more than one target pressure levels can be applied during subsequent passes of the balloon through the lumen. At a minimum, the method of the invention requires two different pressure levels to determine the elastic modulus of the tissue as the ratio of volume and pressure increments. When the pressure increments are relatively small, the radius R vs. additional pressure $\Delta P$ dependence is expected to be close to linear as shown by diagram in FIG. 6. The elastic modulus of the tissue E in soft and stiff areas with coordinates $X_1$ and $X_2$ respectfully can be evaluated by the slopes $\alpha_1$ and $\alpha_2$ of R vs. $\Delta P$ graphs in the linear region. Linear proportionality between pressure (force) and the radius increment (deformation) is assumed here. Extrapolating the graphs until intersection with zero or $\Delta P_0$, can be used to determine the value of lumen size $R_{X1}=R_{X2}$ in unloaded or relaxed condition. More than one pressure level targets may be used as long as the pressure does not exceed a safe loading limit for an even more precise determination of lumen parameters.

Figure 7:
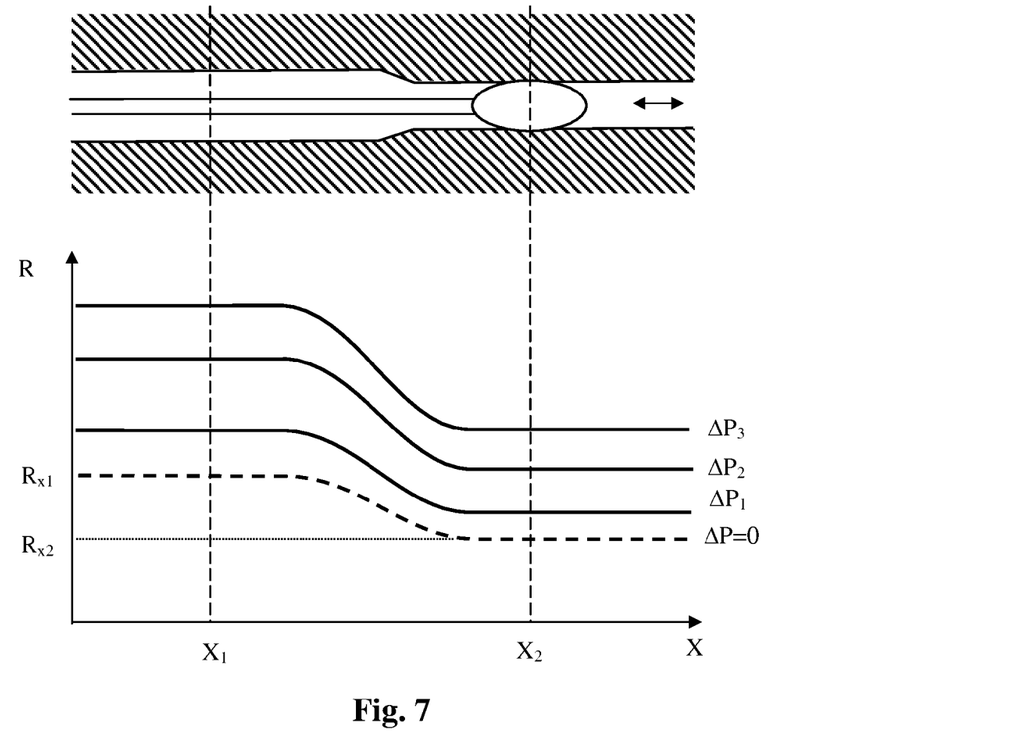
FIG. 7 is a diagram showing changes of balloon's radius during movement along a constant wall stiffness lumen containing two areas of different diameters using a constant pressure evaluation method.
Figure 8:
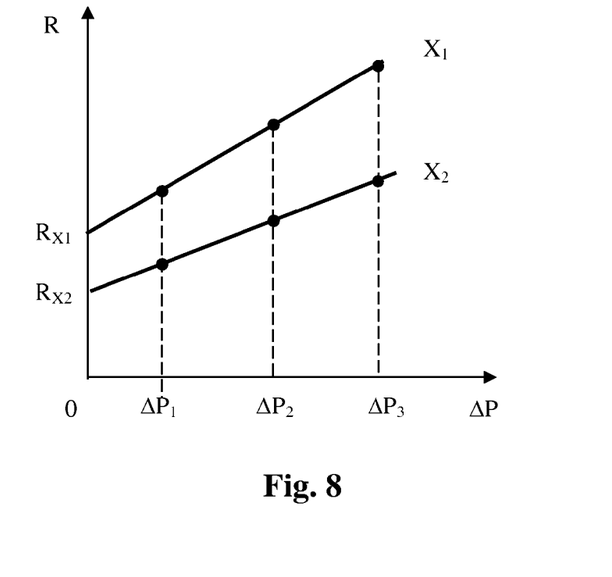
FIG. 8 is a graph of dependence of the balloon's radius on the additional pressure for the evaluation circumstances shown in FIG. 7.

FIG. 7 and FIG. 8 are constant pressure method charts illustrating changes in balloon radius R while the balloon is moved through areas of a constant elasticity lumen having sections of different diameter. Smaller lumen diameter exerts higher pressure on the balloon causing the system to withdraw some fluid so as to adjust the infused volume V and maintain a constant target pressure level. Extrapolating $\Delta P$ vs. R graphs to intersection with zero or $\Delta P_0$ as shown in FIG. 8 allows estimation of the lumen size $R_{X1}$ and $R_{X2}$ at coordinates $X_1$ and $X_2$ respectfully.

Figure 9:
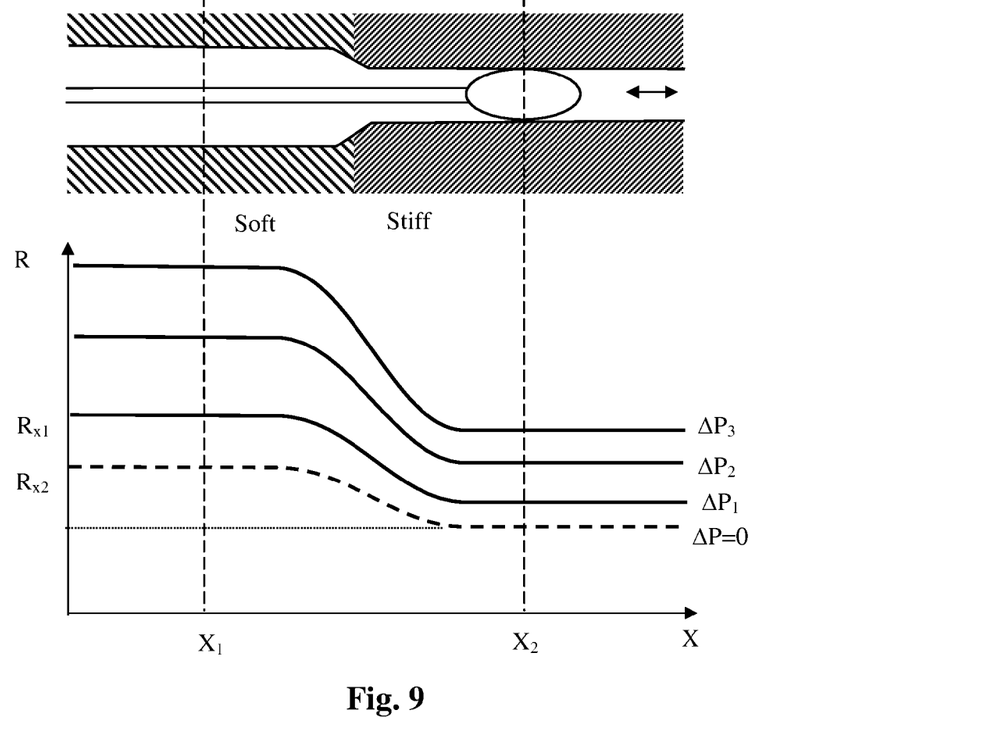
FIG. 9 is a diagram showing changes of balloon's radius during movement along a lumen containing two areas of different diameters and wall stiffness using constant pressure evaluation method.
Figure 10:
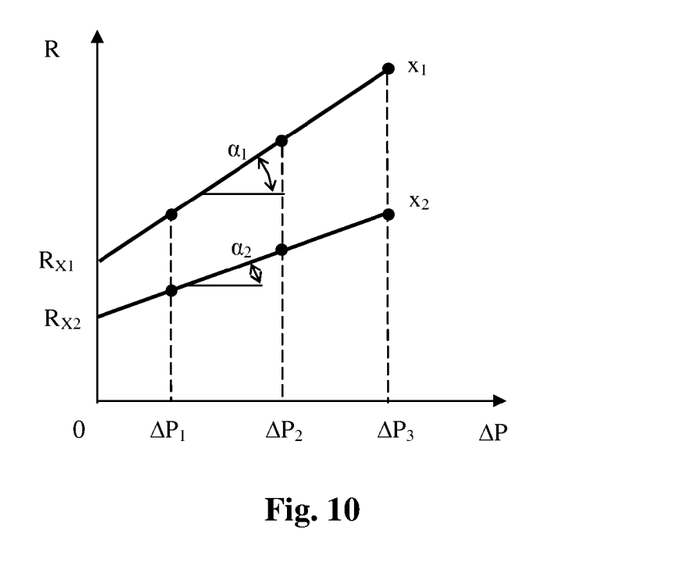
FIG. 10 is a graph of dependence of the balloon's radius on the additional pressure for the evaluation circumstances shown in FIG. 9.

FIG. 9 and FIG. 10 present a complex case, where both elasticity and diameter of the lumen are changing with the stiffer area of the lumen being narrower. As shown in the diagram in FIG. 10, both the size of the lumen at coordinates $X_1$ and $X_2$ and the elastic moduli E at the same coordinates can be estimated from intersections and slopes of R vs. $\Delta P$ graphs.

FIGS. 11 through 16 illustrate the same anatomical cases but the evaluation is done using a constant volume method of the invention. According to that method, at the beginning of the test the balloon 12 is filled with fluid until the pressure sensor shows initial value of $\Delta P$ greater than zero. The balloon at this point just slightly touches the wall of the lumen, thus the radius of the lumen can be calculated in unloaded condition using the empirical calibration curve R as a function of V and $\Delta P$ obtained as described above. During the movement of the balloon, no volume of fluid inside the balloon is changed as compared to the constant pressure method described above. Instead, pressure fluctuations are monitored and recorded as the balloon encounters sections of the lumen wall 100 of varying stiffness and diameter. In that sense, this method is easier to implement as there is no need to constantly inject or remove fluid from the balloon.

Figure 11:
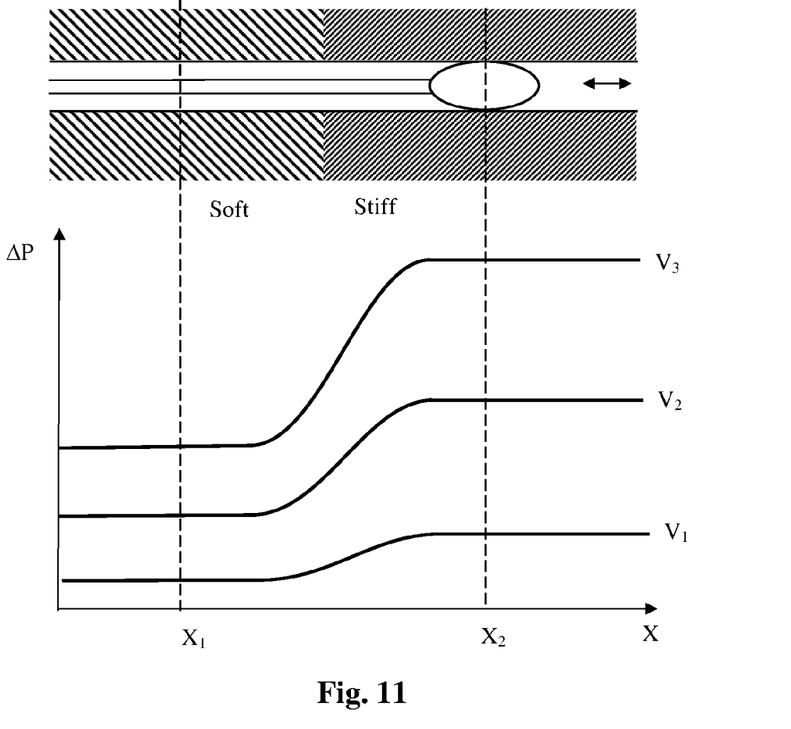
FIG. 11 is a diagram showing changes of balloon's radius during movement along a constant diameter lumen containing two areas of different wall stiffness using constant volume evaluation method.
Figure 12:
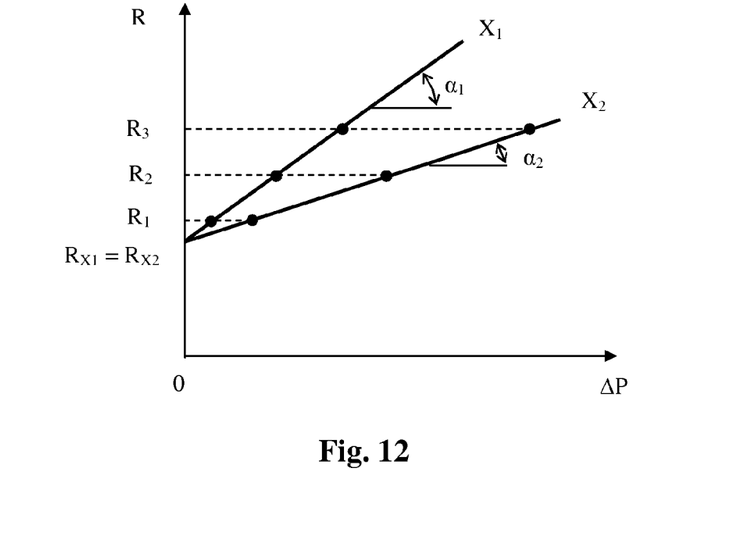
FIG. 12 is a graph of dependence of the balloon's radius on the additional pressure for the evaluation circumstances shown in FIG. 11.

FIGS. 11 and 12 illustrate the evaluation circumstances of the constant diameter lumen having varied stiffness of its walls. When passing through the stiffer area of a lumen, additional pressure $\Delta P$ inside the balloon goes up as compared with the softer areas of the lumen because of lesser deformability of the lumen walls. This is observed at every gradation of the balloon volume V. The relative difference between $\Delta P$ values at different V gradations is proportional to the wall stiffness. Lumen parameters—radius in unloaded condition and the elastic moduli E at different locations—can be determined the same way as in the constant pressure method from R vs. $\Delta P$ graphs created from recorded $\Delta P$ values at different volumes V and using the calibration curve of R vs. V, see FIG. 12.

Figure 13:
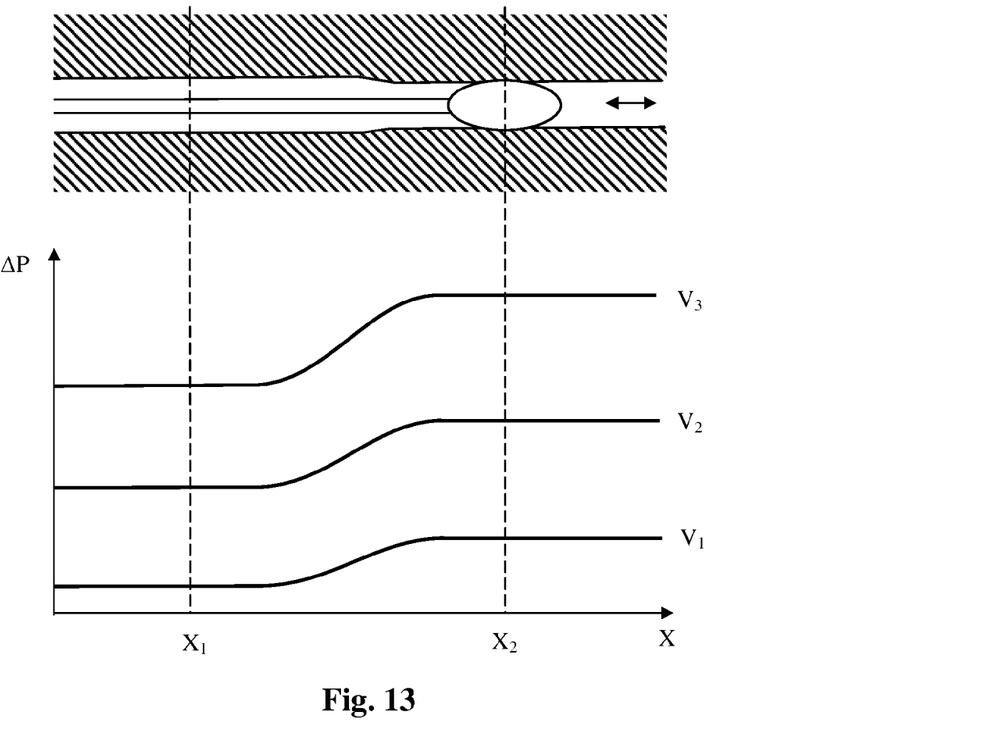
FIG. 13 is a diagram showing changes of balloon's radius during movement along a constant wall stiffness lumen containing two areas of different diameters using constant volume evaluation method.
Figure 14:
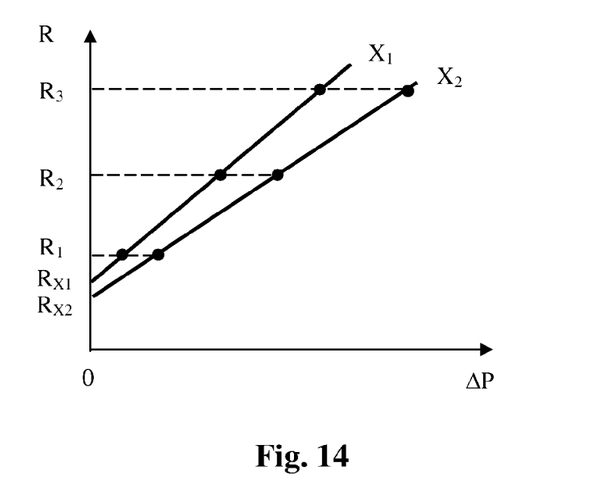
FIG. 14 is a graph of dependence of the balloon's radius on the additional pressure for the evaluation circumstances shown in FIG. 13.
Figure 15:
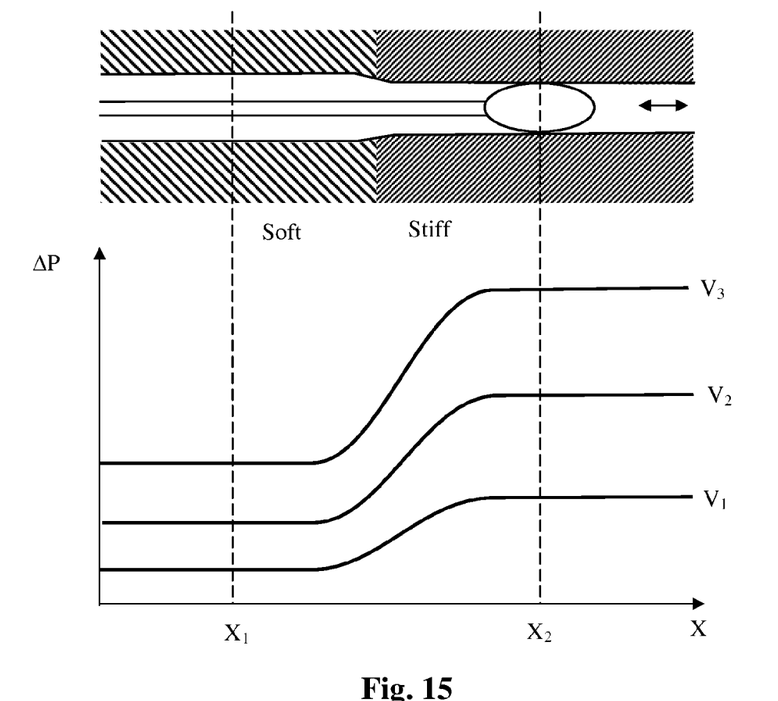
FIG. 15 is a diagram showing changes of balloon's radius during movement along a lumen containing two areas of different diameters and wall stiffness using constant volume evaluation method.

Changes in balloon radius R related to passing through lumen areas of different diameter are illustrated in FIG. 13. The balloon has lower pressure $\Delta P$ when it passes the larger diameter area of the lumen. Similarly to what is described above, lumen radiuses $R_{X1}$ and $R_{X2}$ at respective coordinates $X_1$ and $X_2$ can be determined from R vs. $\Delta P$ graphs at their intersection points with zero $\Delta P$.

Figure 16:
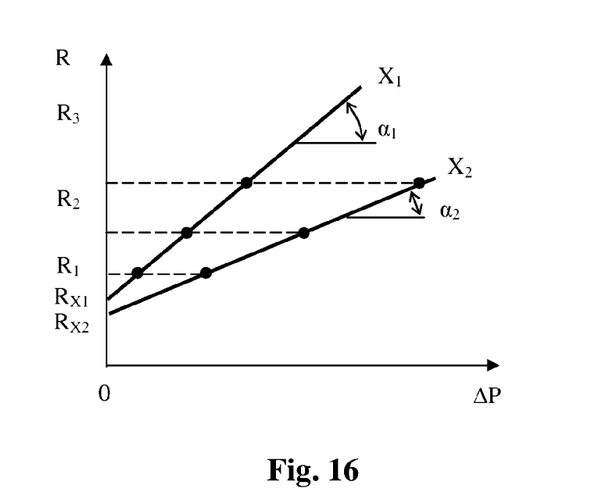
FIG. 16 is a graph of dependence of the balloon's radius on the additional pressure for the evaluation circumstances shown in FIG. 15.

In the combined case of both lumen diameter and stiffness variations (FIG. 15), the lumen radii and the elastic moduli E at certain locations can be determined from R vs. ΔP graphs as seen in FIG. 16. This case differs from the previously illustrated cases where only one parameter (stiffness or diameter) varies, by a notably greater difference between R vs. ΔP slopes at coordinates $X_1$ and $X_2$. Radiuses of the lumen at coordinates $X_1$ and $X_2$ and the elastic moduli E at the same coordinates can be estimated from intersections and slopes of R vs. ΔP graphs the same way as described above in the constant pressure method of evaluation.

The advantage of the constant pressure method is in its safety and preventing of excessive values of applied pressure P to objects of investigation, where diameter of the lumen can vary significantly. Excessive P is eliminated by adjusting the balloon volume V which inherently guards against damage of tissues by inappropriately large size of the balloon. This method works well with organs having lumens with significant variations of their diameter. At the same time, the advantage of the constant volume method is in its relative technical simplicity and potentially faster examination due to no need of continuous volume adjustment during the evaluation procedure. It is most suitable to organs with smaller anticipated deviations of their lumen diameter.

Figure 17:
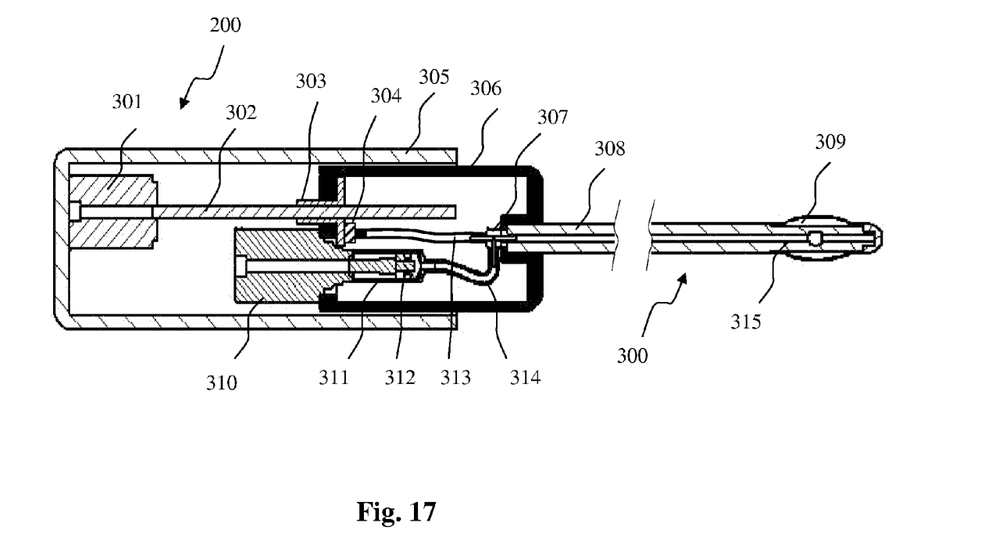
FIG. 17 is a schematic drawing of internal structure of a handheld device for cervix examination, containing balloon inflation, pressure and motion controls and a disposable balloon-tipped probe.

A practical hand-held device 200 adapted to carry out the tissue evaluation according to the present invention is shown in FIG. 17. This device is designed specifically for cervix evaluation. Appropriate adaptation of this device to evaluate other organs and lumens can be devised by those skilled in the art. The device includes a housing 305 shaped and sized for holding by a human hand. a catheter 300 is attached to the device on one end and contains a balloon 309 at its other end. A captive type linear actuator 301 is designed based on a stepper motor and fixedly placed inside the housing 305. It is adapted upon activation of the motor to move the catheter-retaining sliding unit 306 in and out of the housing 305 so as to provide for controlled movement of the balloon 309 inside the lumen of the hollow organ. The movement of the actuator 301 in both directions along a lead screw 302 is achieved by using a lead nut 303 fixed to the sliding unit 306. The length of the movement is determined by the length of the lumen of the hollow organ, in this example the hollow organ being cervix. The sliding unit 305 also includes a second linear actuator 310 of a similar design as the actuator 301. The actuator 310 is adapted to inflate the balloon 309 by moving a plunger 313 of a cylinder 312 used here as a fluid pump. The sliding unit 306 also includes a pressure sensor 304 for measuring pressure of the fluid as well as a three-way connector 307 for separating fluid flows from the pump to the balloon 309 and pressure sensor 304 using tubes 314 and 315.

The catheter probe 300 is a single-use replaceable part of the device that is firmly attached to the sliding unit 306 during operation and contains a rigid catheter tube 308 with an internal channel and an inflatable elastic balloon 309 on the distal end. The tube 308 contains a fluid distributing opening 316 for inflation of the elastic balloon 309. Non-elastic balloons may also be used for the purposes of the invention but they are less advantageous as their inflated diameter is limited. The fluid pump composed of the cylinder 312 with the plunger 313, the probe 300 with the catheter 308 and the balloon 309 and the pressure sensor 304 together form a sealed hydraulic circuit. The linear actuator 310 with the attached cylinder 312 and the plunger 313 is adapted to control the inflation or deflation of the balloon 309 to the desired volume or pressure. In a portable version of the device, an electronic data acquisition and processing unit as well as a power unit comprising batteries can be also placed in the housing 305. Alternatively, the data can be transmitted wirelessly or via cable to a desktop control and data acquisition unit (not shown).

Figure 18:
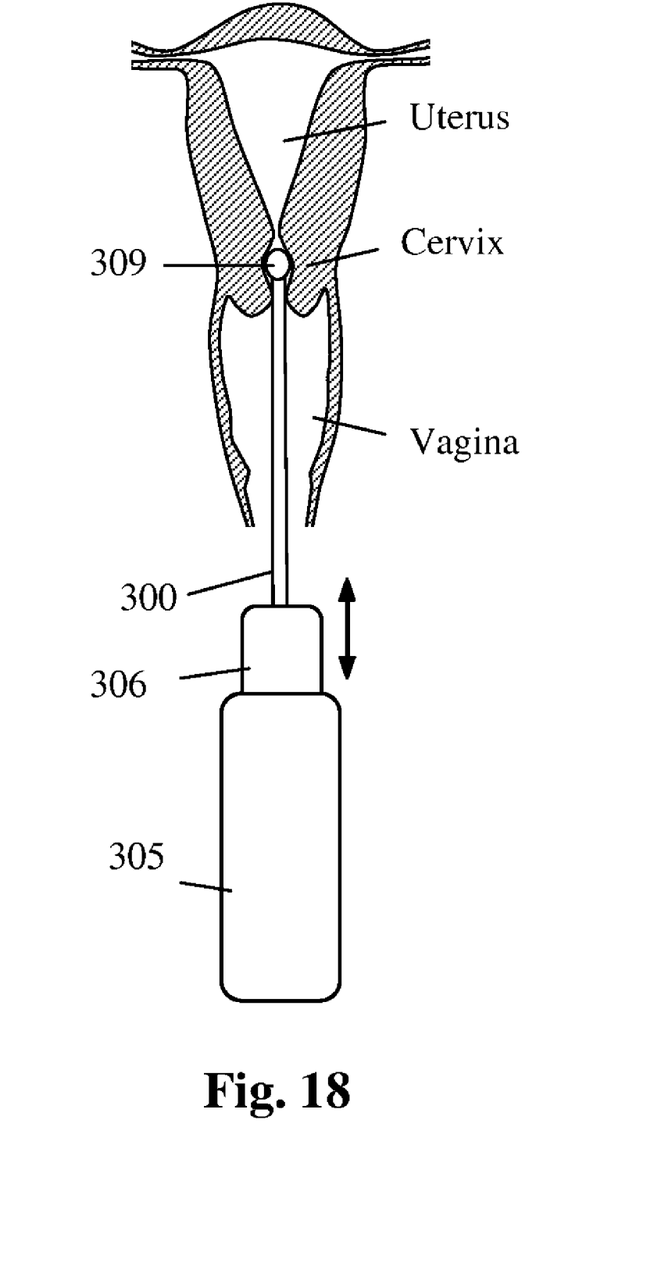
FIG. 18 is a schematic illustration of examination of cervix with a balloon-tipped tube and a handheld device.

The diagram of evaluating cervix in females using the system of the invention is presented in FIG. 18. During a gynecological investigation, the catheter 300 is inserted through the vagina into the cervix of the uterus. A rigid tube containing the balloon 309 may be used to improve pushability of the balloon up the cervix. The balloon 309 is inflated to a predetermined volume followed by controlled movement of the balloon along the lumen of the cervix as performed by motor-guided displacement of the sliding unit 306 relatively to the housing 305 of the handheld device, which is held in a fixed position. The elasticity profile of the cervix is obtained by recording of one or preferably two or more ΔP profiles at different volumes V as a function of the linear coordinate X along the cervix using the corresponding number of runs along the lumen of the cervix.

Figure 19:
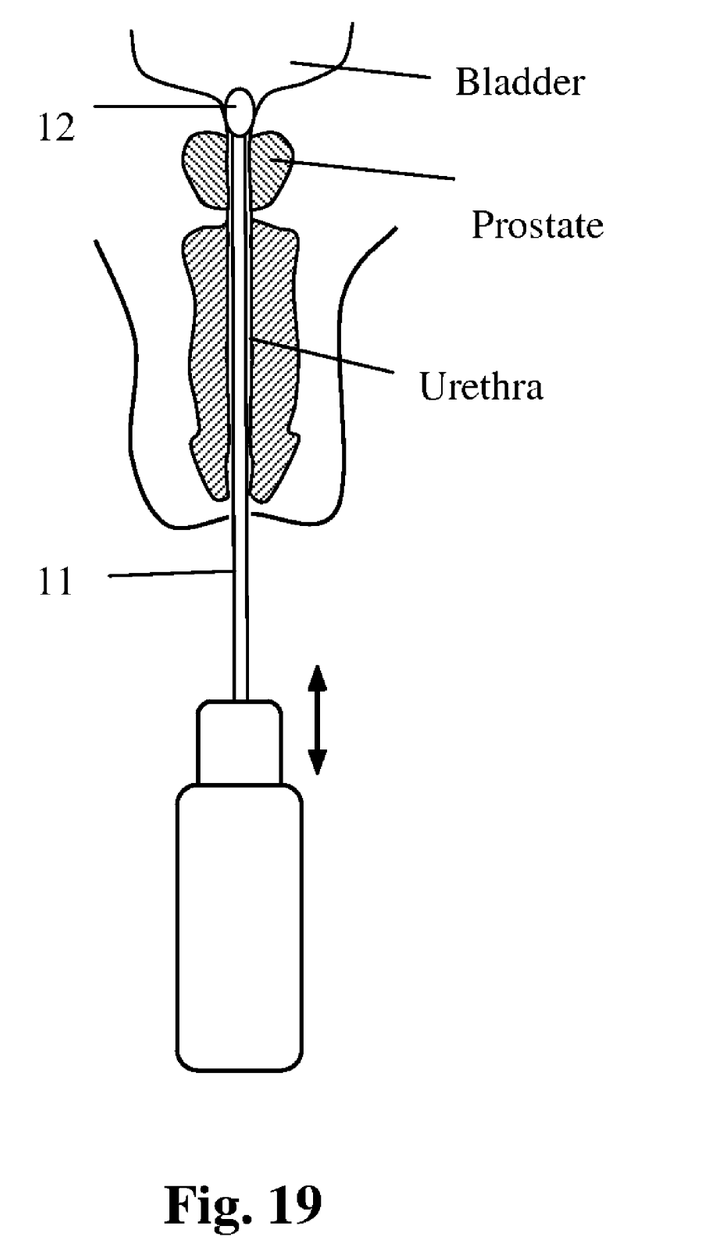
FIG. 19 is a schematic illustration of examination of male urinary tract and prostate with a balloon-tipped catheter and a handheld device.

Another application of the handheld device of the invention is illustrated in FIG. 19. It is aimed at evaluating male urinary tract and prostate. It differs from the gynecological modality described above by using a flexible catheter 11 instead of a rigid tube as well as by selecting both the catheter 11 and the balloon 12 with different geometric and mechanical parameters. The length of examined distance of the lumen is also different and is selected to be appropriate for operation inside the urethra. The urological version of the device can utilize a commonly-used disposable balloon-tipped catheter, for example a Foley catheter.

In operation, the catheter 11 is manually inserted along the urinary tract until the balloon 12 reaches the urinary bladder. The catheter 11 with the balloon 12 are then moved back from the bladder outlet towards the prostate. The initial infused volume of the balloon 12 is selected so that the balloon just slightly touches the walls of the urethra, which is indicated by a small increase in the balloon pressure. The catheter 11 is then pulled straight by holding the device with small tension so as to provide for linear movement of the balloon when the device is activated. Automatic acquisition of ΔP vs. R profiles along the urethra is performed by one of the above described methods, either a constant pressure method or a constant volume method. The opening of the urine bladder into urethra can be used as an easy to detect reference point to set a zero coordinate in tracking the balloon 12. After the first pass of the balloon along the urethra, it is returned back and inflated to the next level of constant pressure P or volume V for another pass through the organ. After accumulating data from two or more runs along the urethra, the system calculates the results in terms of the elastic modulus E, diameter of the channel or other mechanical and elastic properties of the urine tract.

Figure 20:
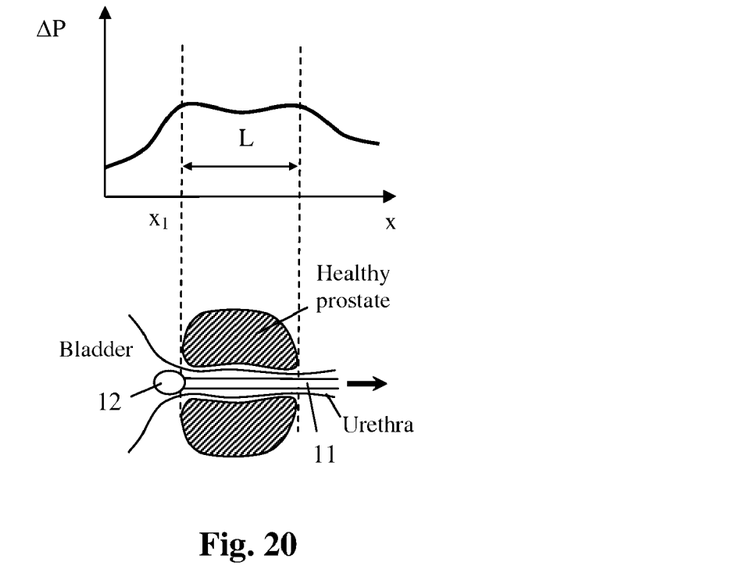
FIG. 20 is an example of a pressure profile of a healthy prostate.
Figure 21:
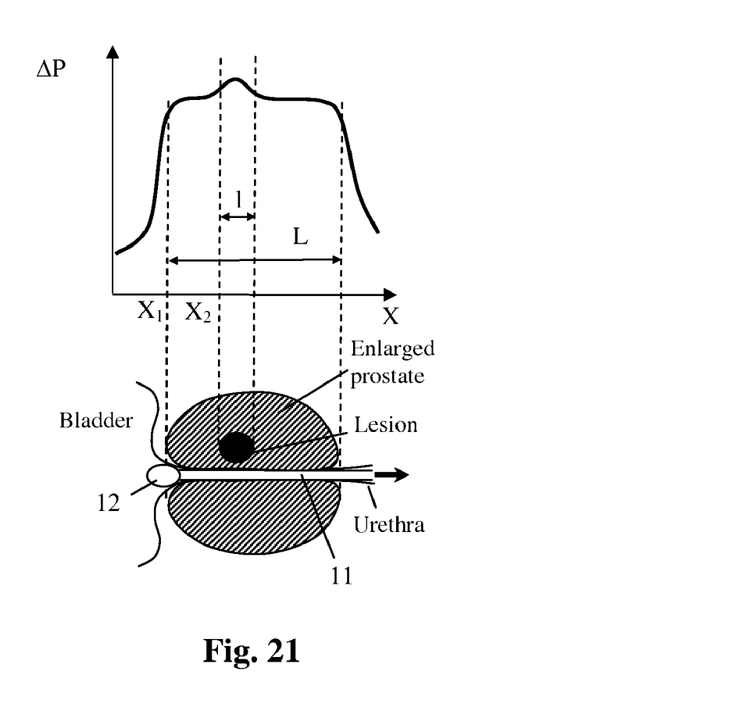
FIG. 21 is an example of a pressure profile of an enlarged prostate with an inclusion.

FIG. 20 and FIG. 21 present two illustrations of exemplary investigation results from a healthy and an enlarged prostate. The amplitude of ΔP response at a constant volume of the balloon is higher in the case of enlarged prostate (FIG. 21), which is a result of both narrowing of the urethra lumen and stiffening of the tissues surrounding the balloon, i.e. the symptoms of the benign prostate hyperplasia (BPH). The shape of ΔP profile can also be used for diagnostic purposes—it is typically uneven due to a higher stiffness of the lumen region located inside the prostate compared to softer marginal regions in the healthy prostate. This is represented by section l in FIG. 21. Presence and location of inclusions, such as local hardenings and lesions, can be detected from the ΔP profile as local increase of ΔP over the basic line. Thus, the method can be potentially used for early diagnostics of tumors and prophylactics of the prostate cancer. Size of the prostate L can be determined from well-defined steep increments of ΔP at entering and leaving the prostate by the balloon 12.

Simultaneous varying of the balloon pressure and volume during examination is also contemplated by this invention. This more complicated method of evaluation may be used with hollow organs in which diameter and stiffness vary abruptly and significantly. In this case, the entire length of the lumen may be divided for the purposes of evaluation into several regions and region-specific evaluation profile may be used for each of these regions. When the balloon is moved from one region to the next, additional fluid volume may be infused or removed to provide the new basis for evaluation.

Although the invention herein has been described with respect to particular embodiments, it is understood that these embodiments are merely illustrative of the principles and applications of the present invention. For example, this disclosure refers mainly to a liquid- or gas-filled balloon which is moved along the lumen of a hollow organ in order to measure its mechanical properties. Mechanically-expanded catheter tips may afford similar properties as liquid-filled balloons. Various wire cages and meshes can be mechanically expanded to varying degree so as to impart similar outward forces on the surrounding organs and tissues. In that case, balloon volume may be replaced with the balloon radius and balloon pressure may be replaced with the cage compression force. Moving a mechanically-expanded tip along the lumen of a target organ is therefore considered to be within the scope of the present invention.

It is therefore to be understood that numerous modifications may be made to the illustrative embodiments and that other arrangements may be devised without departing from the spirit and scope of the present invention as defined by the appended claims.

What is claimed is:

1. A method for determination of structural and elastic properties of a hollow organ containing a lumen traversing therethrough, the method comprising the steps of:
   a) providing an inflatable balloon inside said lumen,
   b) inflating said balloon to a predetermined first pressure,
   c) moving said balloon along said lumen,
   d) continuously inflating or deflating said balloon to maintain said first pressure at a constant level during said movement of said balloon along said lumen, and
   e) measuring balloon pressure, balloon volume, and balloon coordinate along said lumen during said movement, whereby a first spatial profile of said structural and elastic properties of the hollow organ along said lumen is determined using said balloon pressure, said balloon volume, and said balloon coordinate along said lumen.

2. The method as in claim 1, wherein said steps (b) through (e) are repeated at a second predetermined pressure of said balloon so as to determine a second spatial profile of said structural and elastic properties of said hollow organ.

3. The method as in claim 1, wherein said steps (a) through (e) are preceded by obtaining a calibration curve for said balloon, said calibration curve comprising a function of balloon volume vs. balloon pressure while said balloon is not restricted to expand freely.

4. The method as in claim 1, wherein said hollow organ is selected from a group consisting of cervix, urethra, intestines, blood vessels, and esophagus.

5. The method as in claim 1, wherein said properties selected from a group consisting of tissue elasticity, Young's modulus, and lumen diameter.

6. A method for determination of structural and elastic properties of a hollow organ containing a lumen traversing therethrough, the method comprising the steps of:
   a) providing an inflatable balloon inside said lumen,
   b) inflating said balloon to a predetermined first volume,
   c) moving said balloon along said lumen,
   d) maintaining said first volume at a constant level during said movement of said balloon along said lumen, and
   e) measuring balloon pressure and balloon coordinate along said lumen during said movement, whereby a first spatial profile of said structural and elastic properties of the hollow organ along said lumen is determined using said balloon pressure, said first balloon volume, and said balloon coordinate along said lumen.

7. The method as in claim 6, wherein said steps (b) through (e) are repeated at a second predetermined balloon volume so as to determine a second spatial profile of said structural and elastic properties of said hollow organ.

8. The method as in claim 6, wherein said steps (a) through (e) are preceded by obtaining a calibration curve for said balloon, said calibration curve comprising a function of balloon volume vs. balloon pressure while said balloon is not restricted to expand freely.

9. The method as in claim 6, wherein said hollow organ is selected from a group consisting of cervix, urethra, intestines, blood vessels, and esophagus.

* * * * *